United States Patent [19]

Davey

[11] Patent Number: 5,770,794
[45] Date of Patent: Jun. 23, 1998

[54] MONITORING APPARATUS FOR MONITORING IMPENDING FAULTS IN THE INTEGRITY OF A COMPONENT OR STRUCTURE

[75] Inventor: Kenneth John Davey, Bassendean, Australia

[73] Assignee: Tulip Bay Pty Ltd, South Perth, Australia

[21] Appl. No.: 530,368

[22] PCT Filed: May 6, 1994

[86] PCT No.: PCT/AU94/00235

§ 371 Date: Sep. 29, 1995

§ 102(e) Date: Sep. 29, 1995

[87] PCT Pub. No.: WO94/27130

PCT Pub. Date: Nov. 24, 1994

[30] Foreign Application Priority Data

May 6, 1993 [AU] Australia ................................. PL8682
Dec. 31, 1993 [AU] Australia ................................. PM3203
Dec. 31, 1993 [AU] Australia ................................. PM3205

[51] Int. Cl.[6] .................................................. G01M 3/26
[52] U.S. Cl. .................................................. 73/37; 73/40
[58] Field of Search .......................................... 73/37, 40

[56] References Cited

U.S. PATENT DOCUMENTS

| 2,393,996 | 2/1946 | Layton ............................................ 73/37 |
| 2,694,924 | 11/1954 | Matlock et al. ............................... 73/37 |
| 3,820,381 | 6/1974 | Thurston . |
| 4,104,906 | 8/1978 | Oertle . |
| 4,135,386 | 1/1979 | Peterson et al. . |
| 4,145,915 | 3/1979 | Oertle et al. . |
| 4,345,457 | 8/1982 | Kuroki et al. . |
| 4,448,080 | 5/1984 | Dressel et al. . |
| 4,683,745 | 8/1987 | Broughman, Jr. et al. . |
| 4,979,390 | 12/1990 | Schupack et al. . |

FOREIGN PATENT DOCUMENTS

15385 8/1993 WIPO ......................................... 73/37

*Primary Examiner*—Hezron E. Williams
*Assistant Examiner*—Daniel S. Larkin
*Attorney, Agent, or Firm*—Ladas & Parry

[57] ABSTRACT

A monitoring apparatus for monitoring impending faults in the integrity of a component or structure in static or dynamic application. The apparatus includes a sealed cavity on or within the component or structure connected to a source of constant vacuum. The connection between the cavity and the source incorporates a device of high impedance fluid flow and a monitor for monitoring the change in pressure between the cavity and the source.

19 Claims, 9 Drawing Sheets

MONITORING APPARATUS FOR MONITORING IMPENDING FAULTS IN THE INTEGRITY OF A COMPONENT OR STRUCTURE

This invention relates to an apparatus which cam be used to facilitate continuous monitoring of the structural integrity of components or structures to provide an early indication of an impending structural fault. The invention has application to both dynamic and static structures.

A significant difficulty in monitoring the structural integrity of a component has been its need to remove the component from service in order to test the integrity of the component.

In the past most methods using fluids for monitoring and testing of components for structural integrity have involved the monitoring of the progress of the movement of a dye or liquid between the surfaces of the component. These methods are not convenient for use continuously when the structure or component is in service and or is located in an in-accessible area. Therefore it is not convenient for continuous data logging or remote monitoring of the component or structure.

Other methods have comprised using gas under pressure or a vacuum such as U.S. Pat. No. 3,820,381 which describes a method of remotely monitoring hollow fasteners formed of material having a low permeability. The method however is not suitable for materials having high permeability and is not practical for general structures.

In addition the use of evacuated spaces for the purposes of monitoring structural integrity is disclosed in U.S. Pats. Nos. 4,104,906; 4,135,386; and 4,145,915. The methods described use a vacuum for monitoring areas of structure of both high and low permeability but not jointly with the one device. In addition the devices disclosed are unsuited to continuous monitoring in circumstances where ambient conditions (such as variation in air pressure with altitude change) can constantly vary and where it is necessary to know when a fault has occurred or is about to occur rather than merely indicating if a fault has occurred.

It is an object of this invention to provide a means which serves to at least partially overcome some of the previously mentioned difficulties of the prior art systems and to facilitate the continuous monitoring of structures to provide an early warning of an impending fault.

The invention provides an apparatus which is able to be adjusted to accommodate for the inherent permeability losses of the material used in the apparatus of the invention and the materials of the installation being monitored and whereby as a result the testing is unaffected by variations in ambient conditions such as pressure, temperature and the like.

A further application of the invention can comprise the monitoring of existing faults by monitoring the structure at projected maximum acceptable limits of the propagation of the fault and providing an indication of such development.

In one form the invention resides in an apparatus for monitoring of impending faults in the integrity of a component or structure in static or dynamic application comprising a sealed cavity on or within the component structure, a source of substantially constant vacuum, a connection between the cavity and the source incorporating a device of high impedance fluid flow and means to monitor the change in pressure between the cavity and the source. According to a preferred feature of the invention the source of substantially constant vacuum comprises a vacuum storage vessel connected to a vacuum pump. The level of vacuum which can be used with the invention can vary from sub-atmospheric to that which is termed "rough" vacuum and which can be achieved utilising a conventional single stage vacuum pump. In numerical terms the vacuum may generally be of the order of 700 to 50 Torr. The main requirement of the vacuum source is that it needs to be able to provide a substantially constant level of vacuum. The magnitude of vacuum will govern the sensitivity of the monitoring means, however with a vacuum beyond approximately one atmosphere the improvements in sensitivity is not significant.

According to a preferred feature of the invention, a plurality of sealed cavities are connected to the source of substantially constant vacuum.

According to a preferred feature of the invention the cavity comprises a labyrinth of chambers provided on and/or within the component or structure.

According to a further preferred feature of the invention, said cavity is formed by applying an element formed of a layer of material which is shaped to define a recess, said element being applied onto the component and/or structure such that said recess defines the cavity between the element and the component or structure.

According to a further preferred feature of the invention, a plurality of cavities are provided on or within the component or structure and each or groups of cavities are connected to the source by a separate connection incorporating said device of high impedance fluid flow.

According to a further preferred feature of the invention, a second cavity or second set of cavities are provided on or within the component or structure, said second cavity or second set of cavities being vented to the ambient conditions of the structure or component.

According to a preferred feature of the previous feature, each cavity is located in close physical relation to a second cavity.

A feature of the present invention is that the system is dynamic whereby the source of vacuum is maintained substantially constant throughout the monitoring period and the system is able to accommodate for known gaseous flow into the cavity throughout the testing period. Furthermore, the volume of the cavity and connection to the device of high impedance fluid flow is small compared to the volume of the source of vacuum and its connection to the device of high impedance fluid flow.

The invention will be more fully understood in the light of the following description of several embodiments of the invention. The description is made with reference to the accompanying drawings of which.

Each of the embodiments of the invention described below and shown in the accompanying drawings are directed to a means for monitoring the structural integrity of components and structures.

Figure 1A:
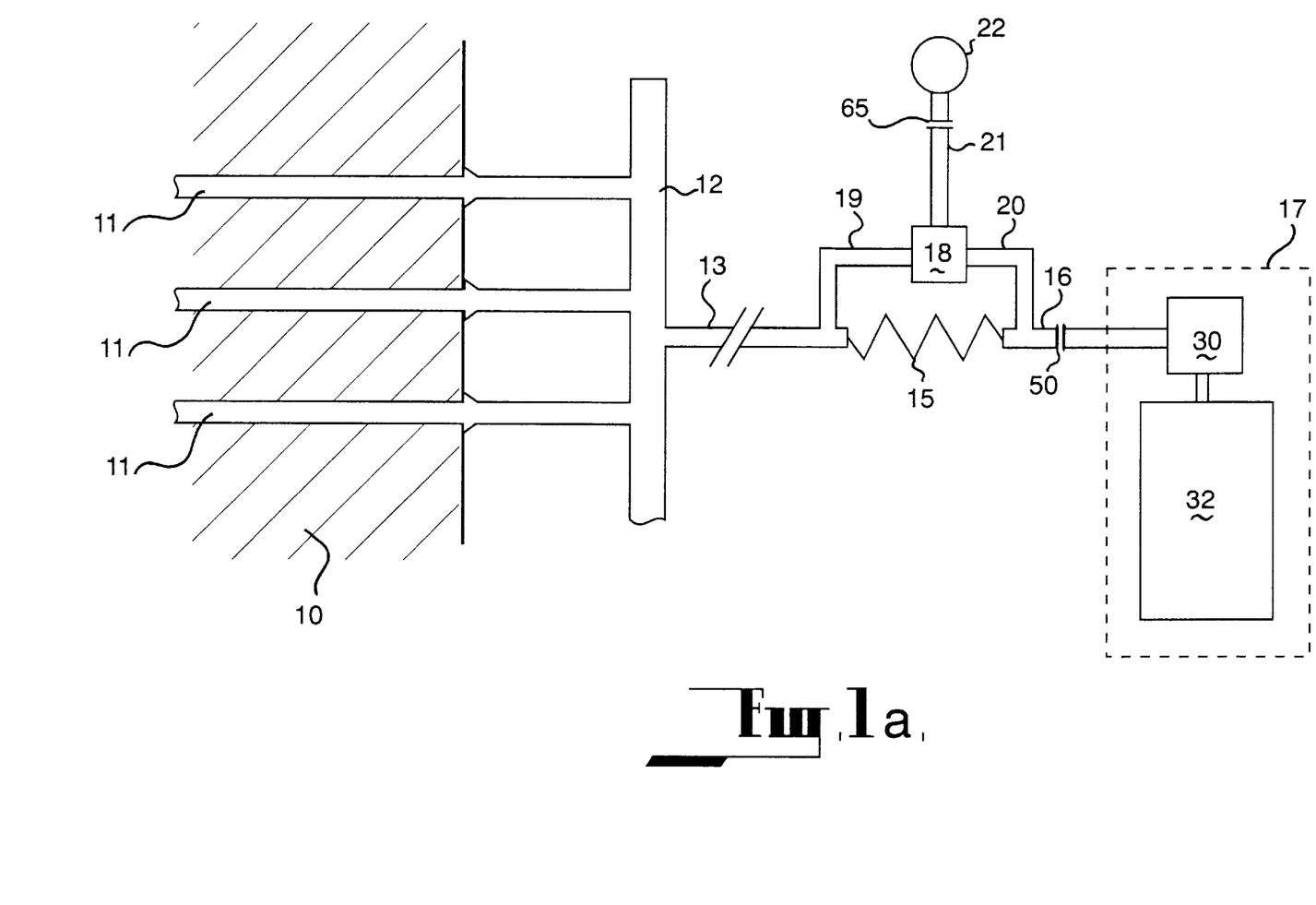
FIG. 1a is a schematic illustration of the first embodiment of the invention.

The first embodiment shown at FIG. 1 relates to a device for monitoring a structure or component which has formed therein a plurality of cavities 11 which extend through or around the region of the component or structure which is to be monitored and each of the cavities has the dimensions of a capillary. Each of the cavities is connected through a manifold 12 to a first duct 13. The first duct 13 is then connected to one end of a high impedance fluid flow device 15 and the other end of the high impedance fluid flow device 15 is connected to a constant vacuum source 17 through a second duct 16.

The constant vacuum source comprises a reservoir 32 having a volume far greater than the combined volume of the cavities 11, the first duct 13 and the manifold 12. The reservoir 32 is connected to a conventional single stage vacuum pump 30 which serves to maintain the level of vacuum in the reservoir 32 substantially constant. This can be achieved by having the pump 30 operated constantly or periodically according to the requirements of the monitoring circumstances. The degree of vacuum which is maintained in the reservoir is generally termed as being a "rough" vacuum.

A differential pressure transducer 18 is connected across the high impedance fluid flow device 15 via connecting ducts 19 and 20 between the first duct 13 and the second duct 16 respectively. The transducer is associated with an electrical output to provide an electrical impulse which is communicated by conductors 21 to a monitor 22 provided at a readably accessible location. The monitor 22 provides an output indicative of an adverse pressure differential being determined by the transducer between the cavities 11 and the constant vacuum source 17 as a result of a significant differential pressure being developed across the high impedance fluid flow device 15.

In the case of the first embodiment being used in a dynamic situation where the component 10 under test is undergoing a cyclic action with respect to a base, the high impedance fluid flow device and transducer may be mounted to the component under test. Therefore the second duct 16 needs to accommodate for such movement by incorporating a rotary seal 50 or the like. In addition, the conductors 21 would need to accommodate for the relative motion between the transducer 18 and the monitor 22 by a dynamic connection 65 such as a slip ring and brush assembly. An example of this arrangement is discussed in relation to the eighth embodiment of FIGS. 7 and 8.

The presence of the high impedance fluid flow device 15 between the cavities 11 and the vacuum source 17 serves to maintain a substantially equal vacuum condition between the cavities and the larger diameter second duct 16 under normal conditions of service. This is because the high impedance fluid flow device has an impedance to fluid flow which is able to accommodate for known gaseous diffusion or anticipated fluid flow into the cavities for the material of which the components are formed together with the manifold 12, first duct 13 and the connections therebetween. In the event of there being an increase in the leakage into one or more of the cavities 11 that change will create? a change in the vacuum condition in the first duct 13 which would not be able to be accommodated by the high impedance fluid flow device 15 and the resultant pressure differential between the first and second duct 13 and 16 would then be sensed by the transducer 18.

The monitoring provided by the first embodiment is independent of the ambient pressure conditions in which the component or structure is located. The standard upon which the cavities are judged comprises the pressure condition within the second duct 16 and the constant vacuum source 17. If desired the apparatus can be rendered substantially independent of temperature variations by the use of appropriate compound materials in the construction of the high impedance fluid flow device 15 in accordance with conventional vacuum techniques.

It should be appreciated that the configuration of the cavities 11 can take any configuration to suit the nature of the structure to be monitored and can be associated with a number of differing components in differing locations on that structure.

According to a specific example of the first embodiment, the cavities have the dimension of a capillary and the first duct is a diameter of 0.5 to 1.0 mm, the second duct has a diameter of 2.0 to 3.0 mm and the high impedance fluid flow device comprising a duct with a diameter of 0.001 to 0.5 mm with a length determined by the desired sensitivity of the device. The high impedance fluid flow device in one form comprises a long length of capillary tubing which is wound around a mandrel or the like. The length and diameter of the capillary tubing determines the sensitivity of the device and in practice the length is chosen in accordance with the anticipated leakage which would be normally expected to take place from the cavities 11, the manifold 12, the first duct 13 and the connections thereof, in order that the fluid flow through the high impedance duct 15 from the source of vacuum will accommodate for such expected leakage. As a result there would be no significant pressure differential created between the first duct 13 and the second duct 16 as a result of such leakage.

A specific feature of the system is its ability to self test on starting and no specific procedure is required to test the system. To achieve maximum sensitivity an isolatible bypass line (not shown) can be installed across the high impedance fluid flow device 15 to be in communication with the first and second ducts 13 and 16 respectively to overcome the hysteresis of the pressure transducer 18 during initial evacuation of the apparatus.

To set the apparatus for maximum sensitivity, it may be necessary to eliminate false readings by allowing sufficient time to enable the completion of the out-gassing of solvents in any adhesives used in connecting the cavities, manifolds and first duct before adjusting the setting of the differential pressure transducer 18.

Figure 1B:
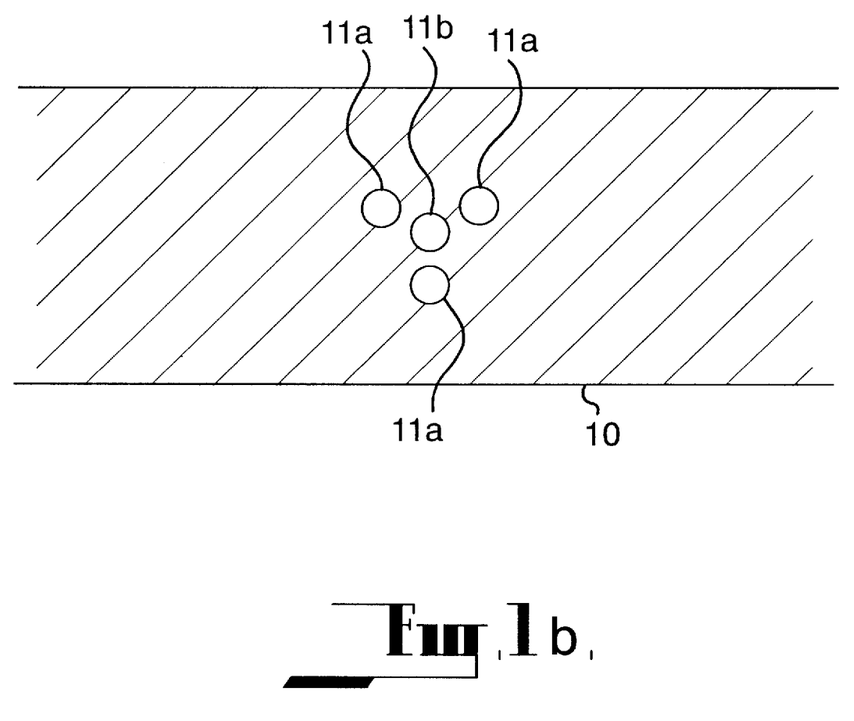
FIG. 1b is a schematic cross-section of a component incorporating a form of the first embodiment.

If desired and as shown at FIG. 1b the cavities 11a may be grouped and may be associated with one or more secondary cavities 11b which are vented to ambient conditions. This arrangement makes it possible to detect the occurrence of faults within a structure before they become visually or otherwise apparent at the surface of the structure.

Figure 2:
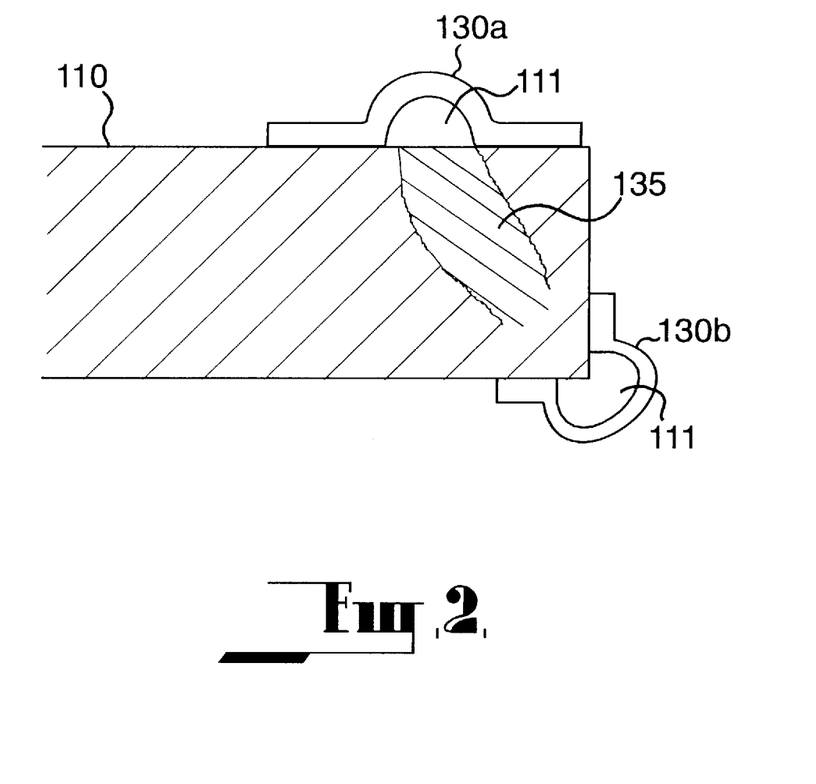
FIG. 2 is a schematic sectional elevation of a structure having a second embodiment applied to it.

The second embodiment shown at FIG. 2 utilises elements 130a and 130b which are applied onto the surface of the component 110 to form a cavity 111 where a portion of the wall of the component 110 forms the cavity 111. The element 130 is formed from a layer of material which is formed with a recess on one face. The material of which the elements 130a and 130b are formed needs to be sufficiently rigid to retain the configuration of the recess and to withstand the pressure differential between the exterior and the interior of the recess when in use. In addition, the material of which the elements 130a and 130b are composed needs to have sufficient ductility such that the recess can be readily formed from the material. The material may comprise metal, plastics or an elastomeric or equivalent synthetic material. In the case of the second embodiment, the elements are formed as a strip, however if desired the element may be formed as a patch or the like.

In the case of the second embodiment as shown at FIG. 2, a pair of strip like elements 130a and 130b are applied to a structure 110 in the region of an anticipated fault 135. One element 130a is applied to a surface of the structure spaced from an edge of the structure while the other element 130b is located at the edge of the structure and is shaped to extend around the edge. The elements 130a and 130b are each connected to a source of constant vacuum through a high impedance fluid flow device (not shown) of the same form as described in relation to the first embodiment of FIG. 1.

On a fault 135 developing and extending to the extent that fluid is able to seep into either of the cavities ill a pressure differential between the cavities and the vacuum source will be created to cause the pressure transducer to be triggered. The sensitivity of the embodiment can be so great that the extent of the fault may not be visually apparent and may comprise a breakdown in the crystalline structure of the material of which the structure is made.

In forming the elements 130a and 130b, a strip of material may be formed by any suitable forming technique, with an elongate groove or recess in the face of each element to be applied to the structure. In addition an adhesive and/or suitable sealing agent is applied to the base to enable each element to be sealingly bonded to the structure.

One form of the elements which are appropriate for use with the second embodiment comprises forming the elements of a plastics tape having an adhesive applied to one face which is covered by a removable protective layer. Prior to application, the tape is formed with the groove. The tape is then cut to the desired length and the protective layer is removed where upon the tape is applied to the structure. One end of the tape is covered by a suitable joiner element to enable connection to the constant vacuum source through the high impedance duct while the other end is sealed off by termination of the groove or by application of a sealant or/an end element.

Figure 3A:
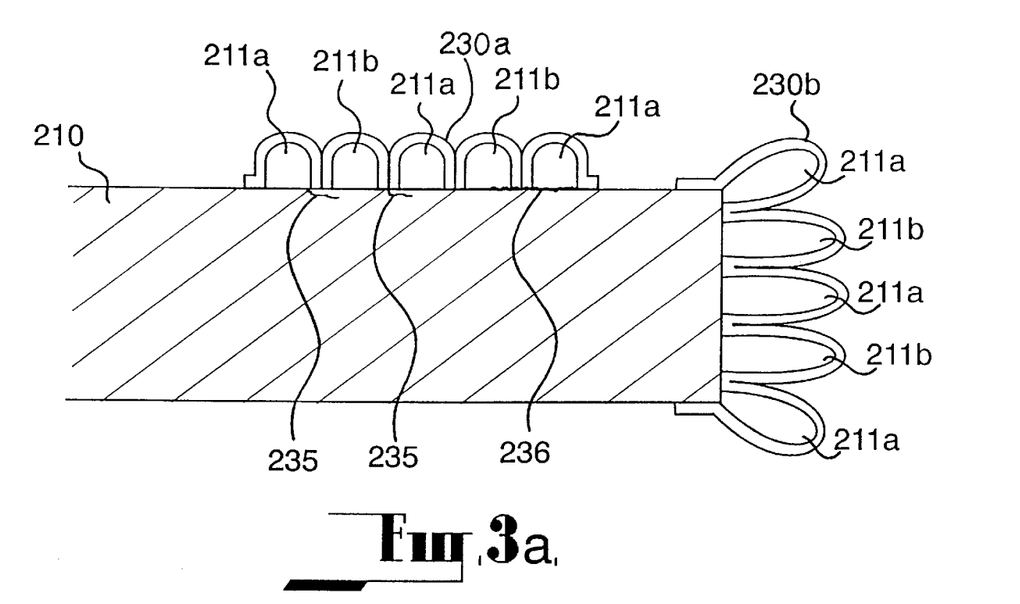
FIG. 3a is a schematic sectional elevation of a structure having a third embodiment applied to it.
Figure 3B:
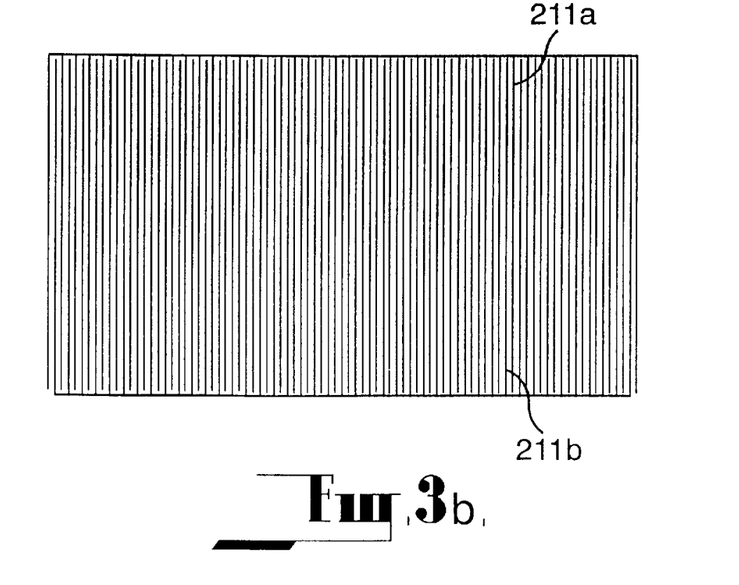

The third embodiment shown at FIGS. 3a and 3b is a variation of the second embodiment and utilizes elements 230a and 230b which are applied to the surface of the structure 210 to form a plurality of cavities 211 over that surface. In the case of the third embodiment the elements 230a and 230b takes the same form as the elements 130a and 130b of the second embodiment with the exception that a plurality of separate parallel recesses or grooves are formed along the length of the elements to form a plurality of parallel cavities 211 with the surface of the structure. The element 230a and 230b are applied to the structure in the same manner as the elements 130a and 130b of the second embodiment and as shown at FIG. 3 can be applied to a face or an edge of the structure 210. In the case of the third embodiment, each of the cavities 211 may be connected to the constant vacuum source as in the case of the second embodiment. Alternatively the outer and central cavities 211a may be connected to the constant vacuum source through the high impedance fluid flow device and the intermediate cavities 211b may be vented to ambient conditions. This arrangement serves to provide a monitoring in relation to surface fractures 235 or surface coat deformation or deterioration 236, that may be expected in the vicinity at the surface of components such as components formed of high alloy materials under cyclic stress.

Figure 4:
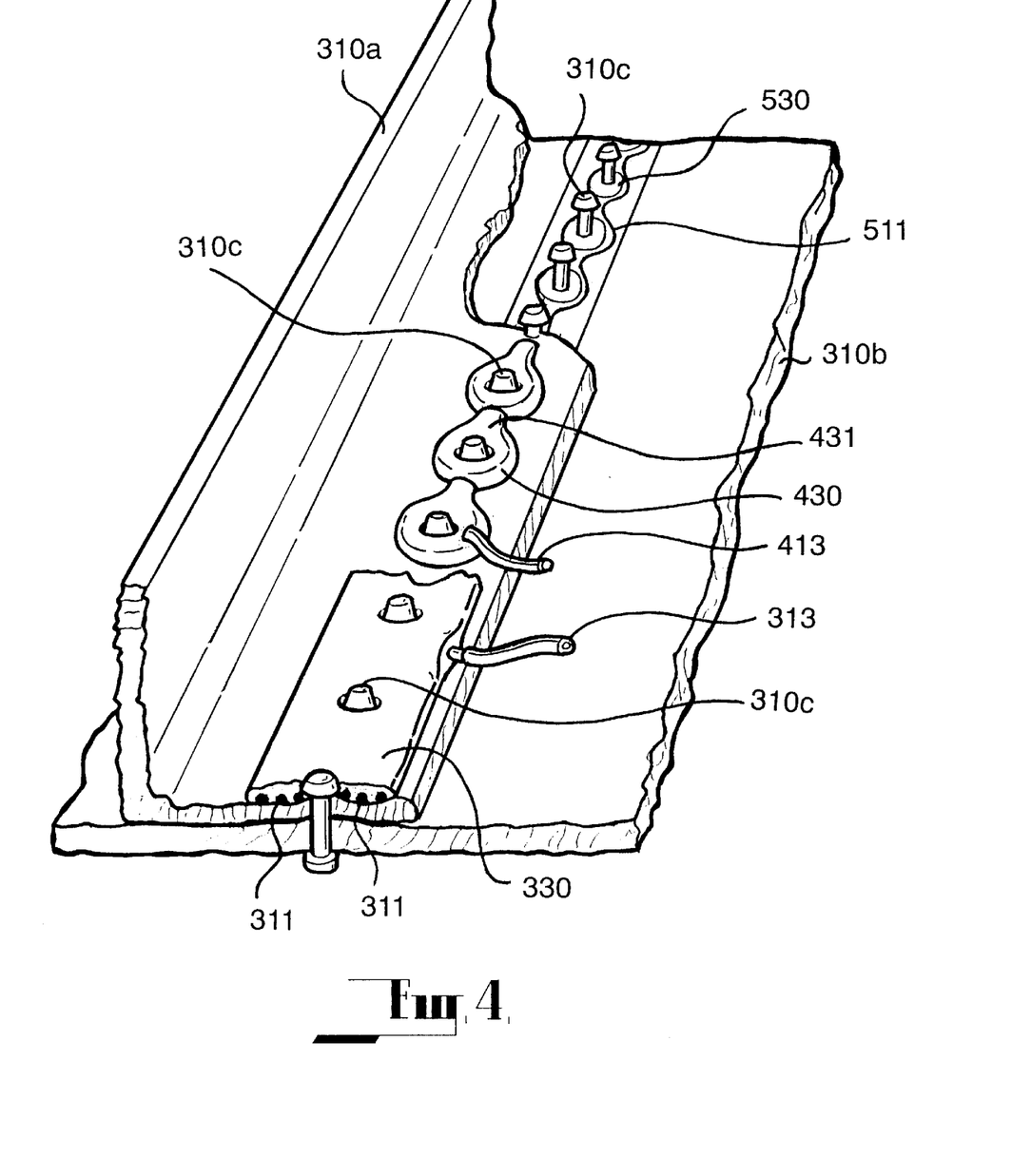
FIG. 4 is an isometric view of a structure having fourth, fifth and sixth embodiment applied thereto.

The fourth, fifth and sixth embodiment are shown at FIG. 4 and each relates to a means for monitoring a riveted joint between two components 310a and 310b which are fixed together by rivets 310c.

In the case of the fourth embodiment, an element 330 of similar form to the elements 230a and 230b of the third embodiment is applied over one face of the joint 310. The element 330 is formed with a set of central axially spaced apertures to enable it to be received over the heads of the rivets 310c and the cavities 311 formed by the element and the surface of the one component 310a are connected to the constant vacuum source through the high impedance fluid flow device and through a first duct 313 as discussed in relation to the first embodiment.

In the case of the fifth embodiment, specially formed segments 430 are applied around each rivet 310c. Each of the segments are annular in configuration to enable them to be received around the rivets 310c and are formed with a radial extension 431 which will be engaged with the adjacent segment (if present). Each segment is formed with an annular recess (not shown) which communicates with a pair of diametrically opposed radial recesses (not shown). When in position the radial recess of adjacent segments will align with each other to provide communication between the cavities defined by each of the segments. The outermost of the segments is adapted to enable connection of the first duct 413 to the cavity formed by the recesses in each of the segments.

In the case of the sixth embodiment a gasket 530 is interposed between first component 310a and the second component 310b. The gasket is formed with a central recess or gallery to form a cavity 511 which extends around each rivet 310c and also extends between several of the rivets. The recess or gallery opens to each face of the components 310a and 310b. This may be achieved by a porous element.

Figure 5:
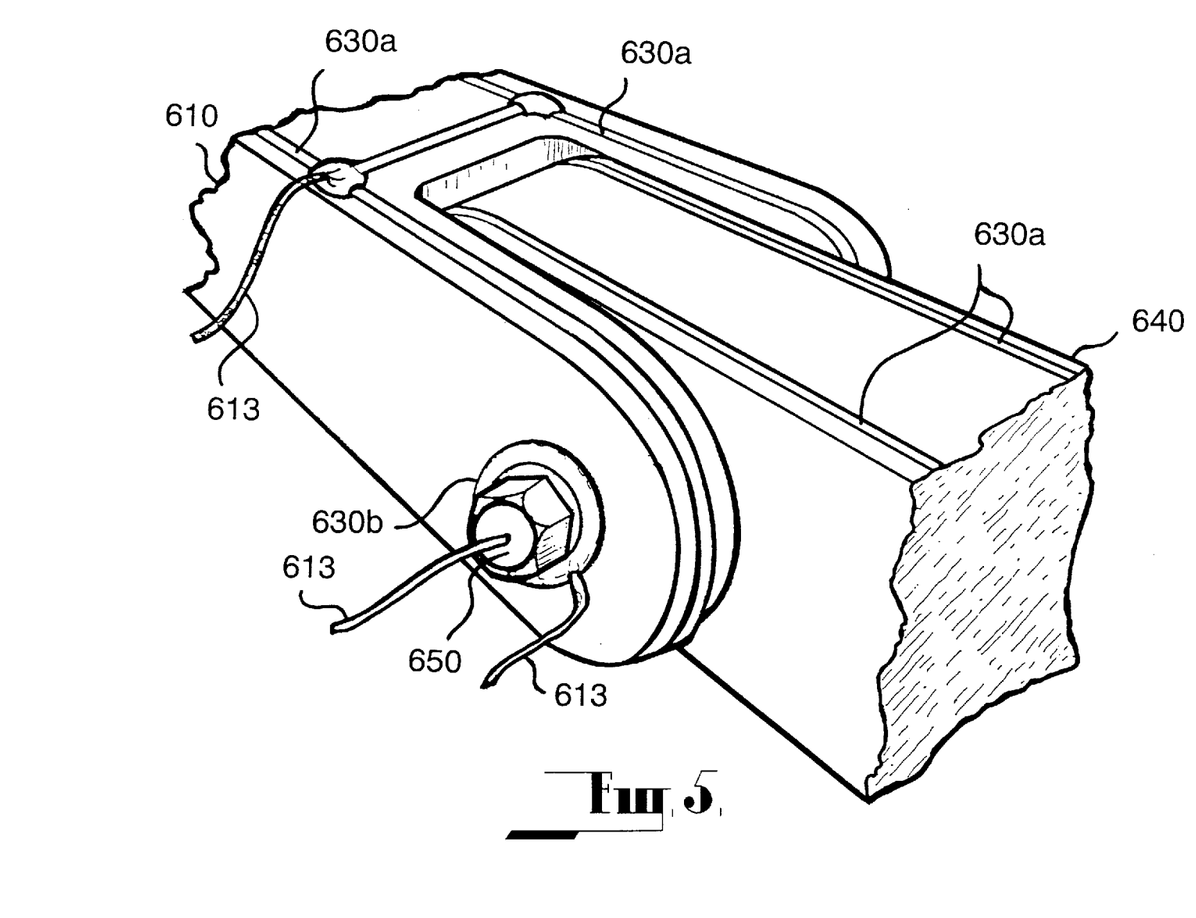
FIG. 5 illustrates an application of the first and second embodiments to a hinged connection between two elements.

FIG. 5 illustrates the application of the first and second embodiments to an installation comprising a hinged connection between two components 610 and 640 through a pivot pin 650. Each of the components has applied to its outer surface a network of elements 630a conforming to the elements 230a and 230b of the second embodiment. In addition the pivot pin 650 is formed with a central axial hole (not shown) of capillary dimensions which defines a cavity in the pivot pin. Furthermore each end of the pivot pin is associated with an annular element 630b of similar form to the element 230a and 230b of the second embodiment and which is fixed to the one component 610 of the hinge connection to surround the pivot pin 650. Each of the elements 630a, 630b and the cavity within the pivot pin 650 are connected to the constant vacuum source through the high impedance fluid flow device by means of first ducts 613.

Figure 6:
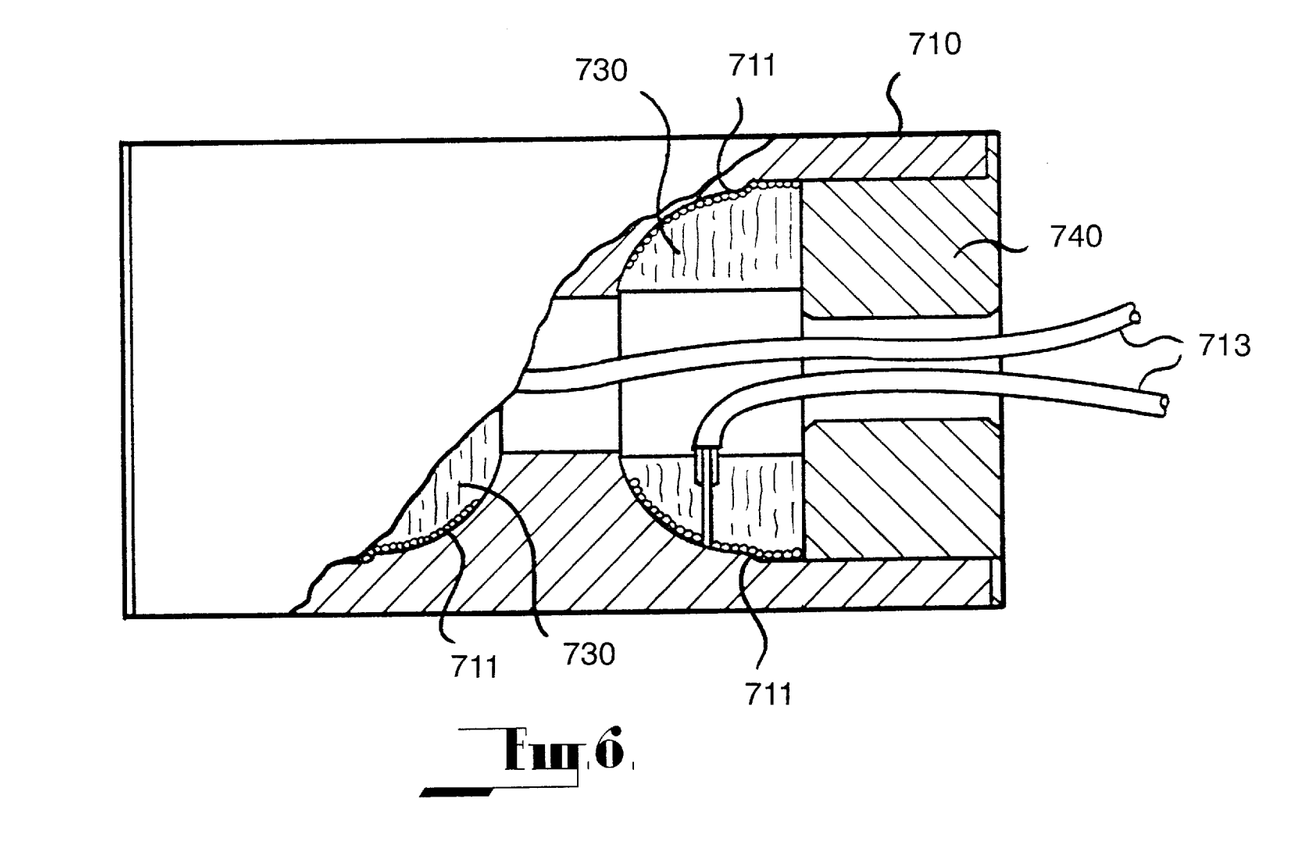
FIG. 6 is a sectional elevation of a aircraft fusible engine mounting pin incorporating a seventh embodiment of the invention.

The seventh embodiment as shown in FIG. 6 relates to means for monitoring the structural integrity of a hollow structural element such as an aircraft fusible engine mounting pin 710. As shown at FIG. 6 the pin 710 is substantially tubular and is provided with end pieces 740 to close each end. The embodiment comprises utilisation of a grommet or like element 730 formed of a plastic or an elastomeric or similar material which has grooves formed in its external face which are able to sealingly engage with the interior face of the pin to form cavities 711 therebetween. The cavities 711 so defined are then connected by first ducts 713 to the high impedance line and constant vacuum source to be monitored as discussed previously in relation to the previous embodiments. As discussed in relation to the third embodiment the cavities 711 may be associated with separate secondary cavities which are co-extensive with the cavities 711 and which are vented to ambient conditions.

In addition, if desired the cavities and secondary cavities may be oriented to be parallel to the central axis of the pin to enable detection of fractures in a shear plane perpendicular to the central axis.

Figure 7:
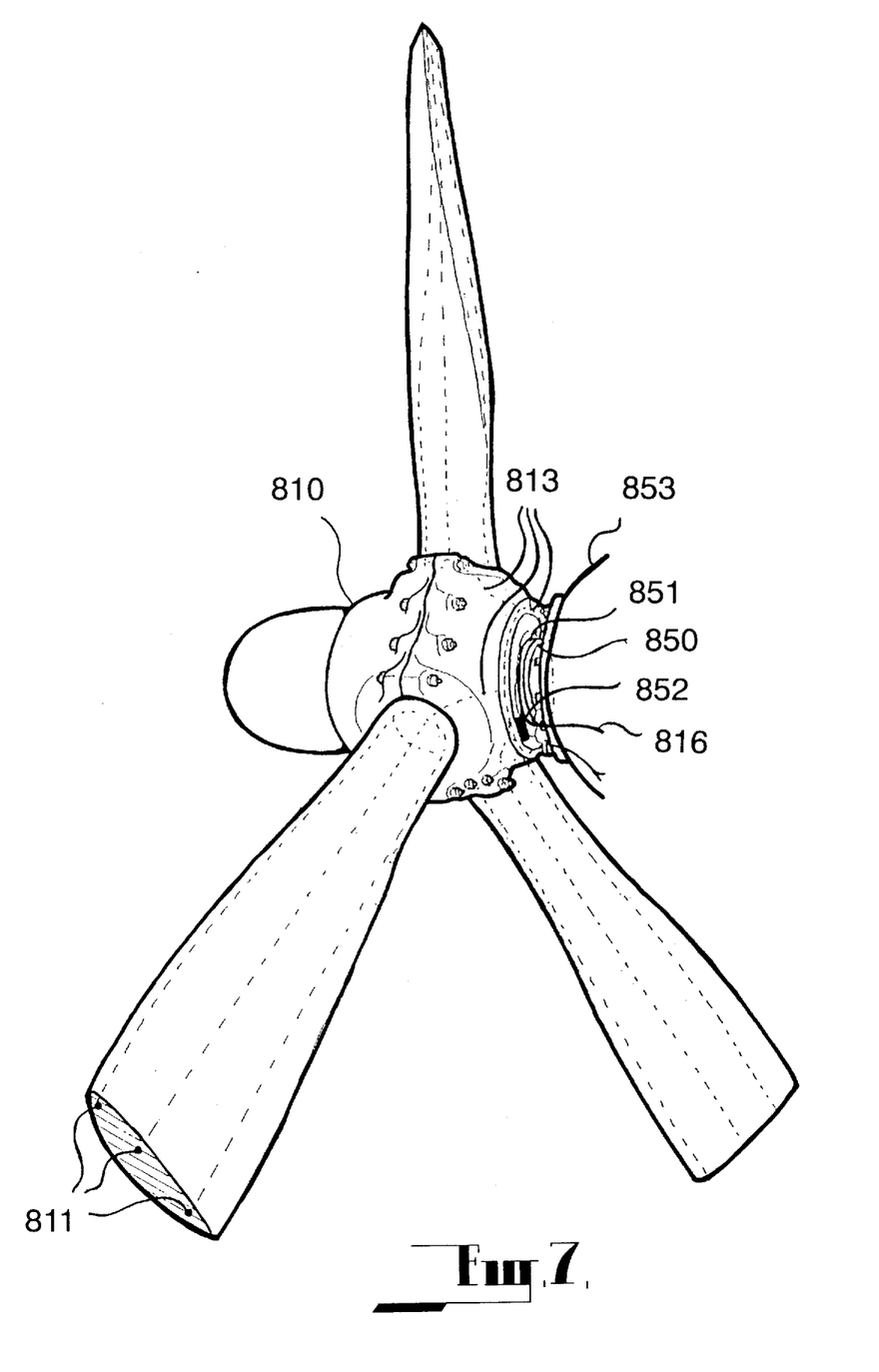
FIG. 7 is an isometric view of an aircraft propeller incorporating an eight embodiment of the invention.
Figure 8:
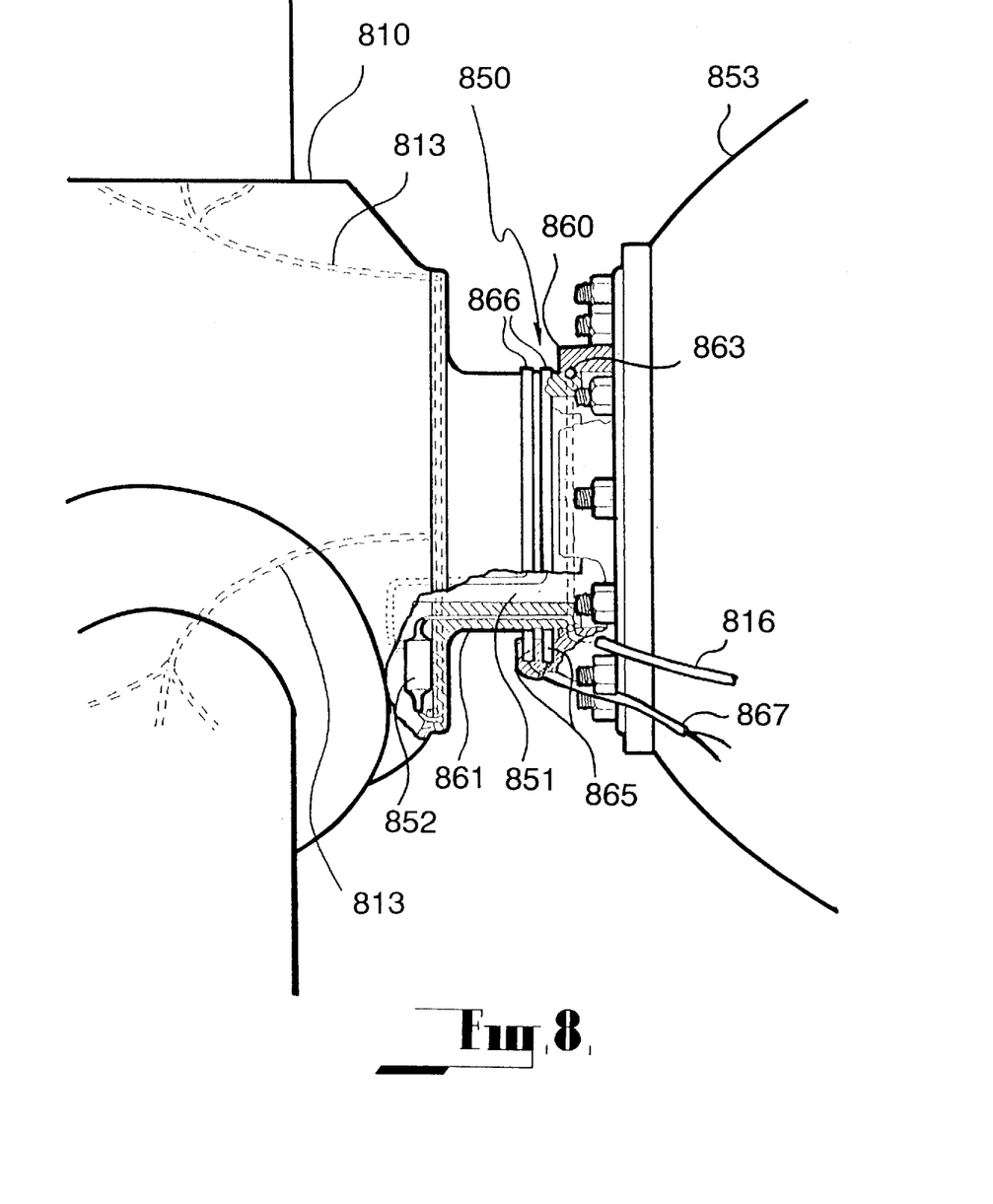
FIG. 8 is a schematic part sectional view of the aircraft propeller mounting shown at FIG. 7.

FIGS. 7 and 8 illustrate the application of the first embodiment as described above in relation to monitoring of the structure of a propeller or airscrew. FIG. 8 illustrates the boss, hub and inner portions of the sectioned blades of an aircraft airscrew incorporating the embodiment. A second duct 816 is mounted to the stationery engine housing 853 and is connected via a rotary seal 850 provided on the propeller shaft 851 to provide fluid communication to a module 852 contained within the hub of the airscrew 810. The module 852 accommodates the high impedance fluid flow device and pressure transducer. The hub is also provided with the small diameter first ducts 813 which connect the cavities 811 which take the form of capillary ducts extending through the propeller blades. If desired the capillary ducts 811 can be replaced with surface galleries formed by modifying electric de-icing boots to provide multiple gallery cavities (not shown) of the form described in relation to the third embodiment.

FIG. 8 illustrates a typical rotary rotating seal 850 to facilitate the vacuum interconnection of the second duct 816 with the module 852. The rotary seal 850 is formed by a first sleeve 860 which is bolted to the static engine housing 853. The first sleeve is concentric with the shaft 851 of the propeller The first sleeve 860 is concentrically receivable over a second sleeve 861 which is fitted over the rotating propeller shaft 851. The second sleeve 861 is attached to the propeller hub. The opposed faces of the first and second sleeves are formed with opposed grooves to form an annular duct 863. Suitable seals are provided on the opposed faces to each side of the duct 863. The second duct 816 opens into the annular duct 863 through the first sleeve 860 and the module 852 is connected into the annular duct 863 through the second sleeve 861. Electrical connection through the transducer is provided by means of rotating slip rings 866 provided on the exterior face of the second sleeve 861 and brushes 865 supported from the first sleeve 860 and which are provided with appropriate electrical conductors 867.

As an alternative to the slip ring and brush assembly, the transducer may be associated with a transmitter and the monitor may be associated with a receiver whereby on the transducer providing a signal indicative of the existence of a pressure differential across the high impedance fluid flow device the transmitter is caused to transmit a signal to the signalling means which will activate the monitor.

In addition, in the case of each of the embodiments where the plurality of cavities being monitored are at different locations on or in a component or structure, the first ducts or manifold ducts from each of the cavities or set of cavities may be capable of being shut-off by a simple clamping action or any other suitable means to serve in isolating the location of a suspected fault in the event of a fault being detected.

For general fatigue testing in the laboratory the invention can be used in testing rigs for remote monitoring of faults or cracks and to enable the shut down of the test equipment at the critical stages of the fault or crack development. In the fatigue testing of high alloy material, the development progress of fine surface fractures which can lead to rapid failure can be remotely detected and tracked by utilising a matrix of small elements in the form of patches or suction cups which are each associated with their own transducer.

In each of the embodiments the volume of the reservoir of the vacuum source is much greater than the combined volume of the cavities, the manifold and second duct.

Examples of application of the invention comprise the monitoring of structures such as airframes, undercarriages, control surfaces, linkages, airscrews, helicoptor rotor assemblies and like structures.

It should be appreciated that the scope of the present invention need not be limited to the particular scope of the embodiment described above.

I claim:

1. An apparatus for the monitoring of impending faults in the integrity of a component or structure in static or dynamic application comprising a sealed cavity on or within the component or structure, a source of substantially constant vacuum, a connection between the cavity and the source incorporating a device of high impedance fluid flow and means to monitor the change in pressure between the cavity and source.

2. An apparatus as claimed in claim 1 wherein the source of substantially constant vacuum comprises a reservoir connected to a vacuum pump.

3. An apparatus as claimed at claim 1 wherein a plurality of sealed cavities are connected to the connection.

4. An apparatus as claimed in claim 1 wherein the sealed cavity comprises a labyrinth provided on and or within the component or structure.

5. An apparatus as claimed in claim 1 wherein the sealed cavity is formed by applying an element formed of a layer of material which is shaped to define a recess which forms the sealed cavity, said element being adapted to be applied to a surface of the component such that the element defines the sealed cavity between the element and the component.

6. An apparatus as claimed in claim 1 wherein a plurality of sealed cavities are provided on a surface of the component or between adjacent surfaces of components of the structure and each sealed cavity or groups of cavities are connected to the source by a separate connection.

7. An apparatus as claimed in claim 1 wherein a second cavity or second set of cavities are provided on a surface of the component or structure, said second cavity or second set of cavities being vented to the ambient conditions of the structure or component.

8. An apparatus as claimed at claim 7 wherein each cavity is located in close physical relation to the second cavity or one or more of the second set of cavities.

9. An apparatus as claimed in claim 1 wherein the volume of the sealed cavity is significantly less than the volume of the source.

10. An apparatus as claimed in claim 1 wherein the component or structure is capable of a cyclic motion with respect to a fixed structure and wherein the source is provided on the fixed structure.

11. An apparatus as claimed at claim 10 wherein the device of high impedance fluid flow is mounted to the component or structure.

12. An apparatus as claimed at claim 10 wherein an interconnection between the source and sealed cavity is effected through a rotary seal.

13. An apparatus as claimed at claim 11 wherein the means to monitor the change in pressure comprises a transducer connected to each side of the device of high impedance fluid flow and which is mounted to the component or structure and a signalling means mounted to the fixed structure, the connection between the transducer and signalling means accommodating for movement between the component or structure and the fixed structure.

14. An apparatus as claimed in claim 1 wherein a second cavity or second set of cavities are provided within the component or structure, said second cavity or second set of cavities being vented to the ambient conditions of the structure or component.

15. An apparatus as claimed in claim 14 wherein each cavity is located in close physical relation to the second cavity or one or more of the second set of cavities.

16. An apparatus as claimed in claim 1 wherein the sealed cavity is formed by applying an element formed of a layer of material which is shaped to define a recess which forms the sealed cavity, said element being adapted to be applied to a surface of the structure such that the element defines the sealed cavity between the element and the structure.

17. An apparatus as claimed claim 1 wherein a plurality of sealed cavities are provided on a surface of the structure and each sealed cavity or groups of cavities are connected to the source by a separate connection.

18. An apparatus as claimed in claim 1 wherein the sealed cavity is formed by applying an element formed of a layer of material which is shaped to define a recess which forms the sealed cavity, said element being adapted to be applied between adjacent surfaces of components of the structure such that the element defines the sealed cavity between the elements and the adjacent surfaces of the structure.

19. An apparatus as claimed claim 1 wherein a plurality of sealed cavities are provided between adjacent surfaces of the components and each sealed cavity or groups of cavities are connected to the source by a separate connection.

* * * * *